(12) United States Patent
Lai et al.

(10) Patent No.: US 10,302,587 B2
(45) Date of Patent: May 28, 2019

(54) TEST STRIP AND METHOD OF OPERATION THEREOF

(71) Applicant: BroadMaster Biotech Corp., Taoyuan (TW)

(72) Inventors: Chien-Hung Lai, Taoyuan (TW); Ya-Sian Lin, Taoyuan (TW); Fan-Yu Chen, Taoyuan (TW)

(73) Assignee: BROADMASTER BIOTECH CORP., Taoyuan (TW)

(*) Notice: Subject to any disclaimer, the term of this patent is extended or adjusted under 35 U.S.C. 154(b) by 476 days.

(21) Appl. No.: 15/084,473

(22) Filed: Mar. 29, 2016

(65) Prior Publication Data

US 2017/0284955 A1 Oct. 5, 2017

(51) Int. Cl.
*G01N 27/327* (2006.01)

(52) U.S. Cl.
CPC ..... *G01N 27/3274* (2013.01); *G01N 27/3272* (2013.01); *G01N 27/3273* (2013.01)

(58) Field of Classification Search
CPC .................................. G01N 27/327–27/3274
See application file for complete search history.

(56) References Cited

U.S. PATENT DOCUMENTS

| 2007/0089987 A1* | 4/2007 | Neel ...................... C12Q 1/006 204/403.01 |
| 2008/0145948 A1* | 6/2008 | Menon ................... G01N 21/78 436/164 |
| 2014/0166503 A1* | 6/2014 | Lai ...................... G01N 27/3275 205/782 |

* cited by examiner

*Primary Examiner* — J. Christopher Ball
(74) *Attorney, Agent, or Firm* — Cheng-Ju Chiang

(57) ABSTRACT

Test strip and method of operating thereof are provided. The test strip, from the top down, comprises a cover, an insulating layer, an electrode set, and a substrate. More particularly, the electrode set at least comprises a first electrode, a second electrode, and a third electrode. The insulating layer comprises a track, and the cover comprises an inlet, an indication line, and at least one vent. With the third electrode and the indication line in accordance with the present invention, a user may confirm the operation status of the test strip and the loading status of biological samples with ease to improve the accuracy of testing.

16 Claims, 7 Drawing Sheets

TEST STRIP AND METHOD OF OPERATION THEREOF

1. TECHNICAL FIELD

At least one embodiment of the present invention relates to a test strip for detecting the change in electrochemical properties in biological samples and the method of operating thereof. More particularly, a test strip and the method of operating thereof used to examine the loading amount of biological sample.

2. DESCRIPTION OF THE RELATED ART

Portable test strips for biological samples such as blood glucose test strips provide enormous convenience to users. The users may obtain the blood glucose levels any time and therefore protect the users from some threats to life. As the development of test strips and test devices, the accuracy of commercial products is largely increased. However, these products still provide insufficient reliability to the users.

One of the most common problems is that users are unable to know whether the amount of sample provided to a test strip is sufficient to run a test, since the test strip is minimized to be portable. Insufficient amount of sample frequently leads to errors in the testing, which is a waste of test strips and a threat to secure the life of users.

Another problem is that users are unable to understand whether the test strips has been used. Repeatedly used test strips usually leads to errors in the testing.

Accordingly, there is a need for mechanisms to ensure that the amount of sample is sufficient to run a test and that the test strips are unused.

SUMMARY

At least one embodiment of the present invention provides test strips and the methods of operating thereof. The embodiment is used to detect the temperature, voltage, and the combination thereof from biological samples. The embodiment is also used to ensure that the test results are unlikely affected by the amount of biological samples and used test strips.

The test strip, from the top down, comprises layers including a cover, an insulating layer, an electrode set, and a substrate.

The lowermost layer is the substrate made of polyester. The electrode set is disposed on the substrate, in which the electrode set comprises at least three electrodes. The three electrodes are the first electrode, the second electrode, and the third electrode respectively.

The insulating layer is disposed on the electrode set. The insulating layer comprises a track at one end of the insulating layer, in which the track is configured for observation. Moreover, the track is also configured to define and expose at least three reaction regions. The three reaction regions are the first reaction region, the second reaction region, and the third reaction region respectively. The first reaction region is part of the first electrode located at the outer area of the track, the third reaction region is part of the third electrode located at the inner area of the track, and the second reaction region is part of the second located between the first reaction region and the second reaction region.

The cover is disposed on the insulating layer, in which the cover comprises an inlet, an indication line, and at least one vent. More particularly, the inlet is disposed at one end of the cover close to the track, while the indication line is configured at one end of the track away from the inlet. The at least one vent is configured with the indication line, where is also away from the inlet.

The electrode set in the test strip is configured to detect the amount of biological samples and provide feedback to a detection device as the biological samples fill the reaction regions of the test strip. The electrode set may also provide the signal of repeated use to the detection device as the test strip in use has been previously loaded with biological sample to the reaction regions. The indication line is configured for users to manually confirm of loading status of biological samples in the reaction regions. The designs can be used to reduce the waste to test strips and impact of insufficient sample amount.

At least one embodiment of the present invention provides methods for operating the aforementioned test strips. The methods comprise step A) to engage the test strip with a detection device, in which the detection device comprises a processor and a sensor, step B) to detect a first temperature of the test strip by the sensor, step C) to examine the first temperature by the processor, and step D) to perform step E) if the first temperature is a first predetermined value which indicates that the first temperature matches the working temperature of the system, otherwise performing step K).

The methods further comprise step E) to examine a first voltage of the first electrode by the processor, step F) to perform step G) if the first voltage is below a second predetermined value which indicates that the test strip is unused, otherwise performing step K), and step G) to load a sample and provide a driving voltage to obtain a test result by the detection device and store the test result to the memory unit for step H) if the first voltage is greater than a third predetermined value, otherwise perform step L).

The methods also comprises step H) to examine a second voltage of the third electrode by the processor, and step I) to perform step J) if the second voltage is greater than a fourth predetermined value which indicates that the amount of sample is sufficient, otherwise performing step K), and step J) to display the test result and terminate the testing procedure by the detection device, step K) to display a warning message and terminate the testing procedure by the detection device, and step L) to idle for two minutes and then terminate the testing procedure.

In the methods, step A) to step D) are primarily to examine whether the environment matches the working temperature of the system. Step E) to step F) are primarily to examine whether the test strip is unused. Step G) is primarily to obtain test results, while step H) to step I) are primarily to examine whether the amount of biological samples is sufficient. Step J), step K), and step L) are for the termination of the testing procedure.

The test strips and the methods of operating thereof provide mechanisms for users to confirm the operation status of test strip with ease, as well as to avoid the test strips repeated used and the biological samples in insufficient amount. Therefore, the test strips and the methods of operating thereof can improve the accuracy of testing.

DESCRIPTION OF THE PREFERRED EMBODIMENTS

Figure 1:
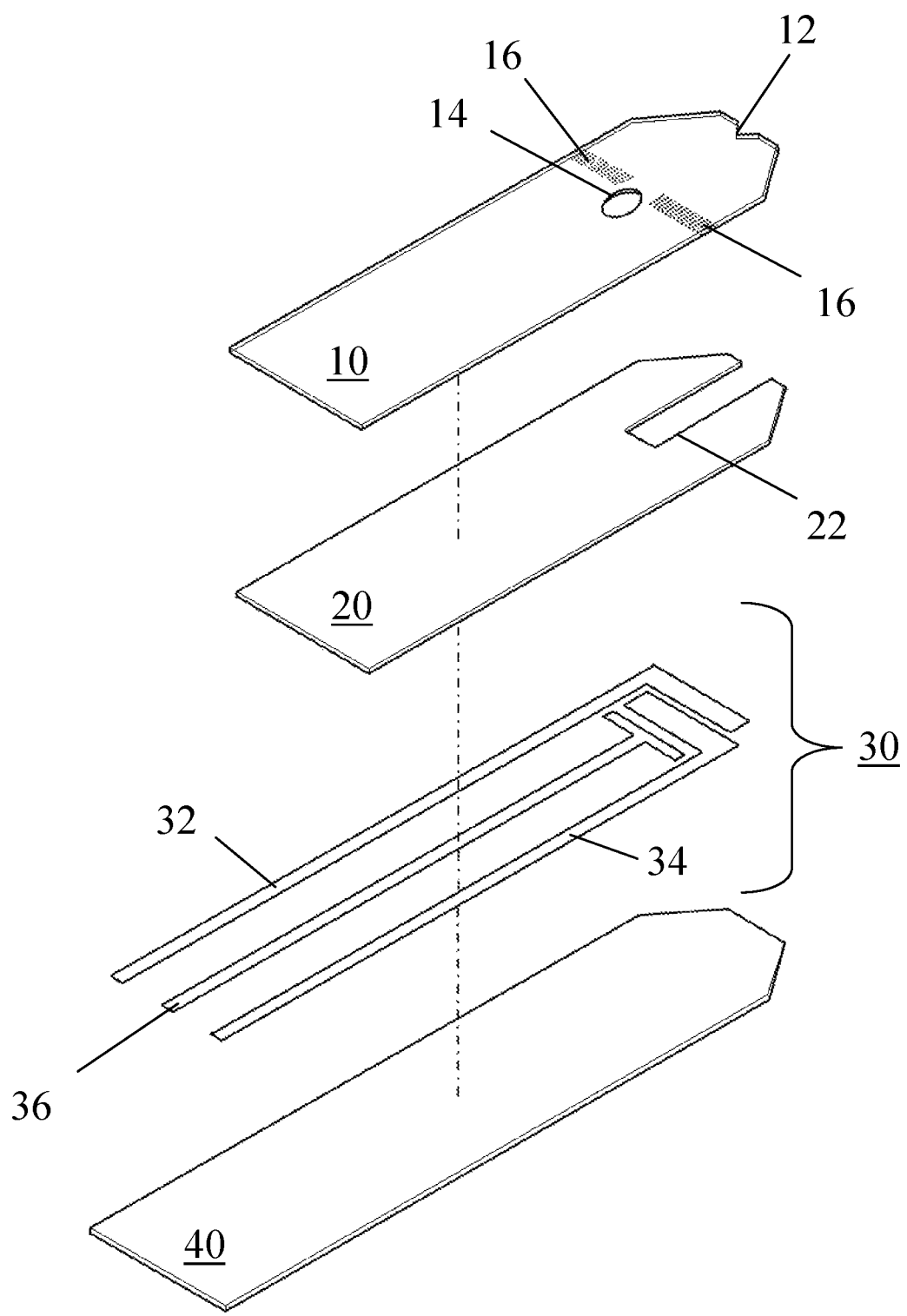
FIG. 1 is the exploded view of a test strip, in accordance with some embodiments of the present invention.
Figure 2:
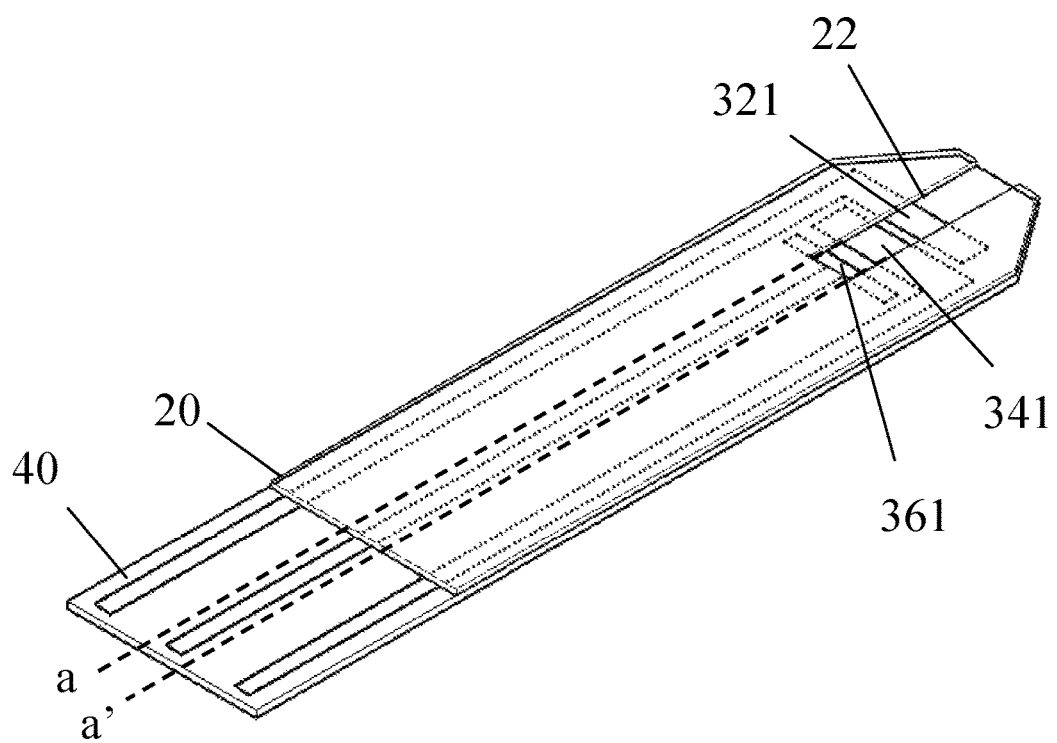
FIG. 2 is the perspective view of a test strip, in accordance with some embodiments of the present invention.

Some embodied test strips and methods of operating thereof are depicted in the following section. Referring to both FIG. 1 and FIG. 2. FIG. 1 is the exploded view of a test strip, in accordance with some embodiments of the present invention. FIG. 2 is the perspective view of a test strip, in accordance with some embodiments of the present invention. The test strip comprises a substrate 40 made of polyester, an electrode set 30 disposed on the substrate 40. The electrode set 30 comprises a first electrode 32, a second electrode 34, and a third electrode 36. In FIG. 1, the first electrode 32 and the second electrode 34 are in L shape, while the third electrode 36 is a T-shaped electrode. More particularly, the first electrode 32 in L shape is configured at the outer area of the substrate 40 as compared to the second electrode 34 and the third electrode 36, and the third electrode 36 in T shape is configured at the inner area of the substrate 40 as compared to the first electrode 32 and the second electrode 34. The short hand of the second electrode 34 is therefore between the first electrode 32 and the third electrode 36 on the substrate 40. On the other hand, the insulating layer 20 is disposed on the electrode set 30 and comprising a track 22 at one end of the insulating layer 20. The track 22 is configured to define the part of the first electrode 32 located both on the substrate 40 and at the outer area of the track 22 as a first reaction region 321 (as shown in FIG. 2), define the part of the third electrode 36 located both on the substrate 40 and at the inner area of the track 22 and indicated by the dash line a and the dash line a' as a third reaction region 361 (as shown in FIG. 2), and define the part of the second electrode 34 located between the first reaction region 321 and the third reaction region 361 as a second reaction region 341 (as shown in FIG. 2). The track 22 is also configured to display the first reaction region 321, the second reaction region 341, and the third reaction region 361 (as shown in FIG. 2). The test strip also comprises a cover 10 disposed on the insulating layer 20. The cover 10 comprises an inlet 12, an indication line 16, and at least one vent 14. Specifically, the inlet 12 is disposed at one end of the cover 10 close to the track 22, while the indication line 16 is configured at one end of the track 22 away from the inlet 12 and the at least one vent 14 is configured with the indication line 16 at the end away from the inlet 12.

One embodiment of the present invention is a test strip for testing blood glucose level. In the embodiment, the first electrode 32 is a working electrode configured to detect blood glucose level, the second electrode 34 is a reference electrode configured to provide the standard electric potential as a reference, and the third electrode 36 is an electrode-based fullness detector configured to examine whether the blood sample is sufficient and have filled the third reaction region 361.

More particularly, the cover 10 in this embodiment is transparent. A user may observe the flow of the blood sample in the track 22 through the cover 10 which is transparent.

The cover 10 is transparent. However, the indication line 16 is further configured on the cover 10 for users to identify whether the flow of blood sample in the track 22 arrives at the place indicated by the indication line 16 through the cover 10. More particularly, the indication line 16 is configured between the end of the track 16 and the at least one vent 14, where is on the third electrode 36 or at the third reaction region 361. The configuration of the indication line 16 is because that the electrode set 30 is hided under the cover 10 and the insulating layer 20, and because the users may not be confident to determine how much blood sample is sufficient.

Figure 3:
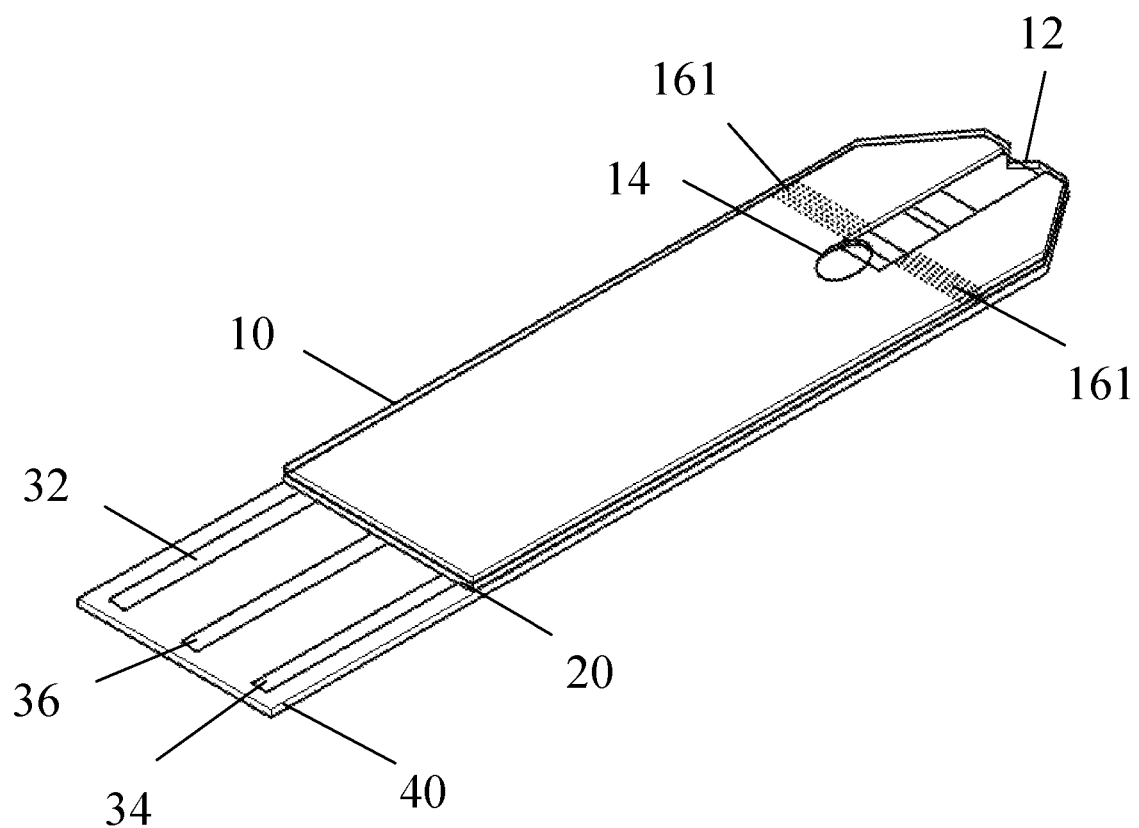
FIG. 3 is the side view of a test strip comprising a first indication line, in accordance with some embodiments of the present invention.

FIG. 3 is the side view of a test strip comprising a first indication line, in accordance with some embodiments of the present invention. The indication line is coated with a dye to form the first indication line 161. The dye may be in yellow, red, blue, and other colors to emphasize the first indication line 161. The configuration of the first indication line 161 is because users may not see the details on the cover 10 as they are under low blood glucose level or illness.

Figure 4A:
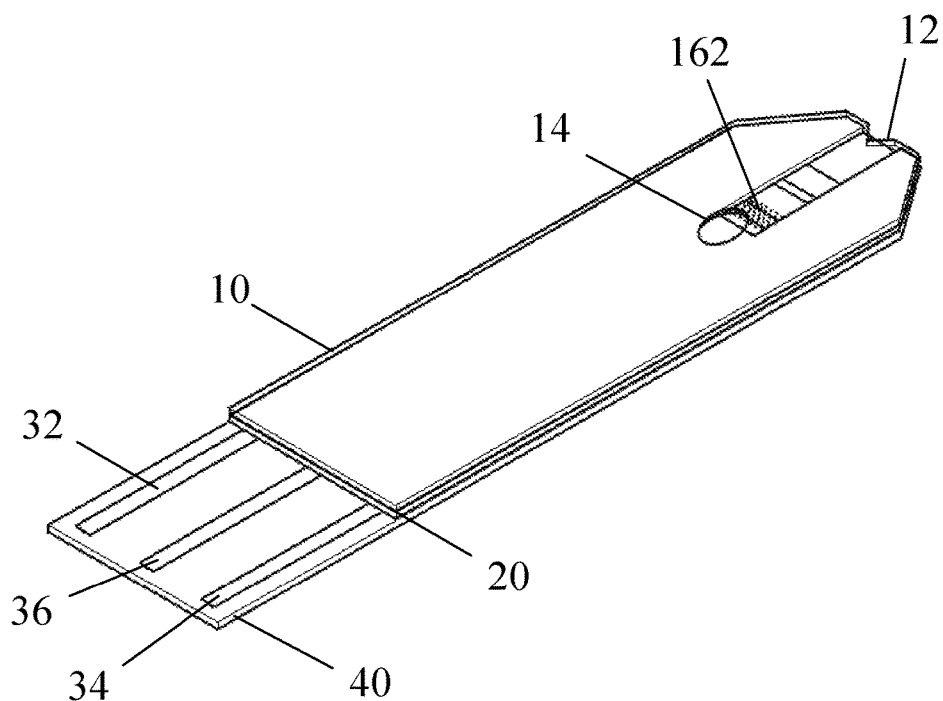
FIG. 4A is the side view of a test strip comprising a second indication line, in accordance with some embodiments of the present invention.
Figure 4B:
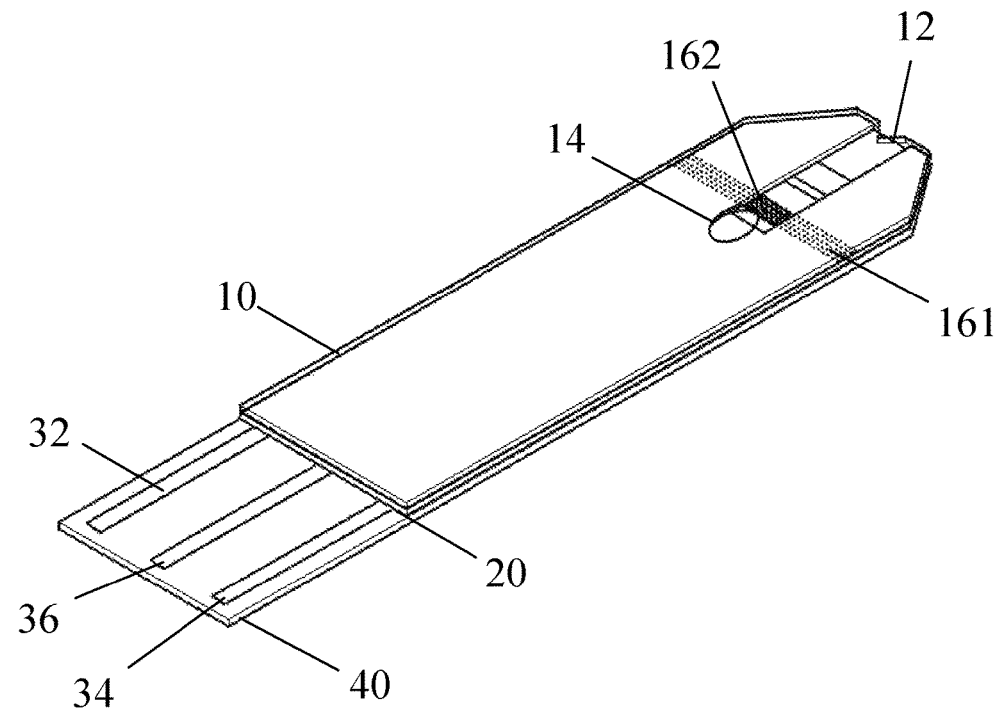
FIG. 4B is the side view of a test strip comprising a first indication line and a second indication line, in accordance with some embodiments of the present invention.

FIG. 4A is the side view of a test strip comprising a second indication line, in accordance with some embodiments of the present invention. The indication line may be fully or partially coated with a color developer to form the second indication line 162. In FIG. 4A, the indication line is partially coated the color developer to form the second indication line 162. FIG. 4B is the side view of a test strip comprising a first indication line and a second indication line, in accordance with some embodiments of the present invention. In FIG. 4B, the first indication line 161 and the second indication line 162 are co-existed, in which the second indication line 162 located between the first indication line 161.

The color developer used for the second indication line 162 comprises 3,3-bis-(4-dimethylaminophenyl)-6-dimethylaminophthalide (crystal violet lactone, CVL), bisphenol A, and cetyl alcohol. In the present embodiment, the color developer is a mixture of crystal violet lactone, bisphenol A, cetyl alcohol, and water. The ratio of crystal violet lactone: bisphenol A:cetyl alcohol:water is 0.2-0.8:10-11:20-22:30-40 in weight percent. The color developer in the present embodiment is temperature sensitive. The color developer changes its color under the range of 35-37° C. For example, the color of the color developer turns from violet into yellow as under 37° C. That is, when the blood sample in regular body temperature (i.e., 37° C.) flows to the second indication line 162, the color of the color developer changes. The change of color signals to users that the blood sample has arrived to the third electrode 36 or the third reaction region 361, which can reduce the problem of providing insufficient amount of the blood sample.

Figure 5:
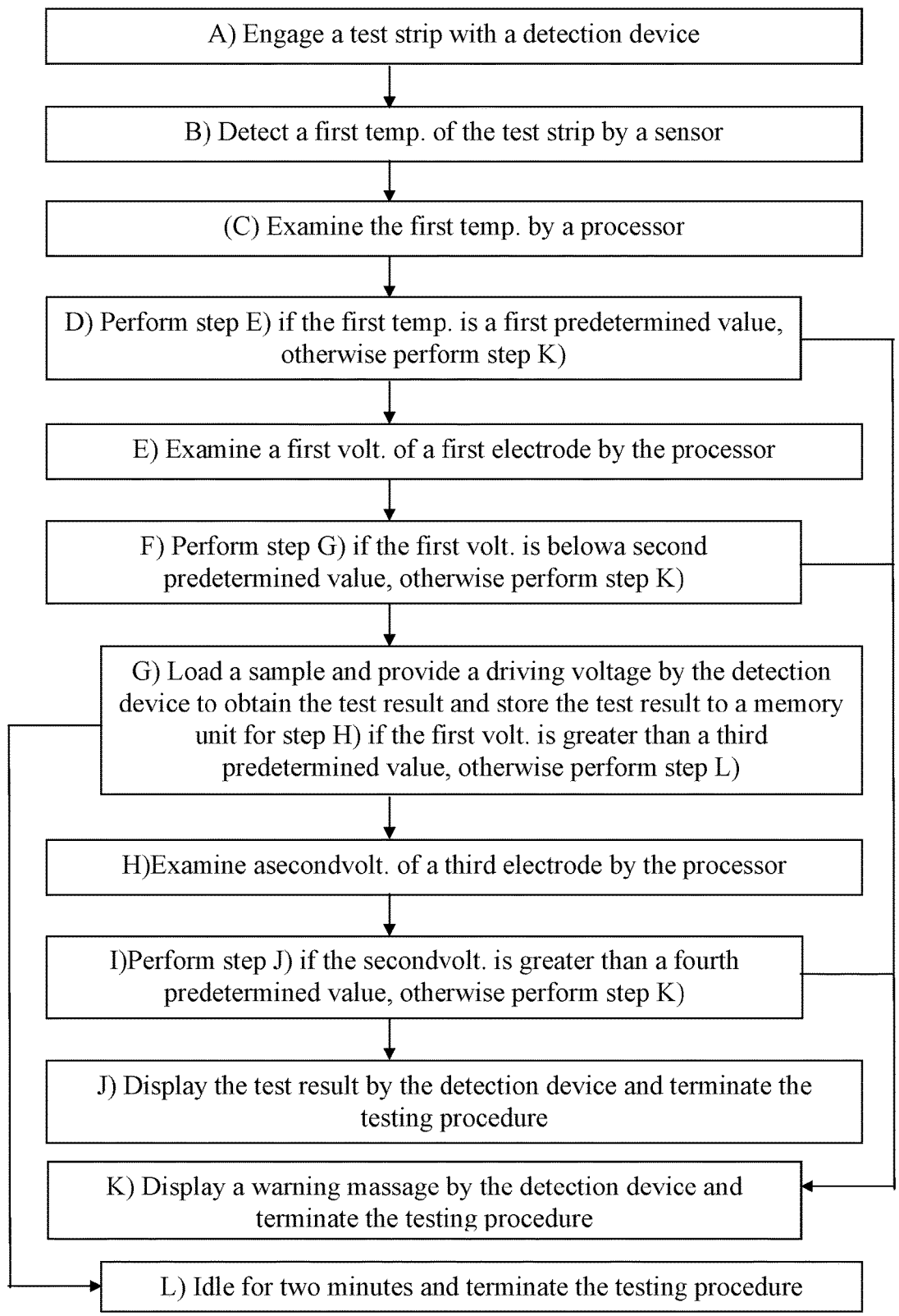
FIG. 5 is the flow chart of a method of operating test strip, in accordance with some embodiments of the present invention.
Figure 6:
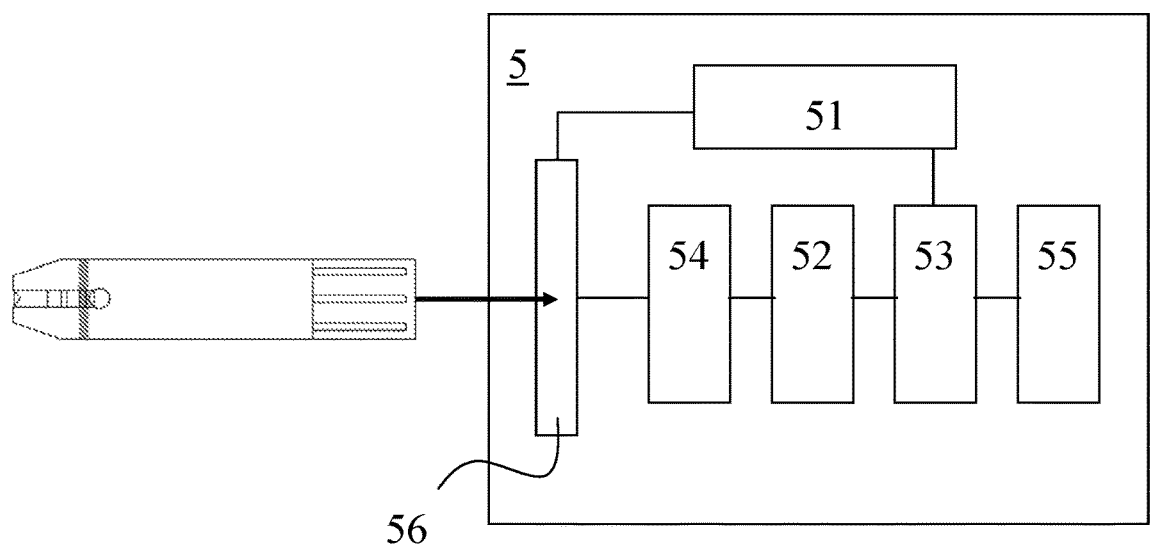
FIG. 6 is a schematic diagram illustrating the detection device, in accordance with some embodiments of the present invention.

At least one embodiment of the present invention is a method of operating the test strip. Referring to FIG. 5 and FIG. 6, in which FIG. 5 is the flow chart of a method of operating test strip and FIG. 6 is a schematic diagram illustrating the detection device. The method comprises step A) to engage the test strip with a detection device 5. The detection device 5 here comprises a processor 52, a temperature sensor 54, a power source 51, a memory unit 53, a display 55, and a connector 56. The method also comprises step B) to detect a first temperature of the test strip by the temperature sensor 54, a step C) to examine the first temperature by the processor 52, step D) to perform step E) if the first temperature is within a first predetermined value (i.e., to examine whether the detected temperature matches the working temperature for the system), otherwise perform step K), step E) to examine a first voltage of the first electrode 32 by the processor 52, a step F) to perform step G) if the first voltage is below a second predetermined value (i.e., to examine whether the test strip is used), otherwise perform step K), step G) to introduce a sample and provide a driving voltage by the detection device 5 to obtain a test result and store the test result to the memory unit 53 for step H) if the first voltage is greater than a third predetermined value, otherwise perform step L), step H) to examine a second voltage of the third electrode 36 by the processor 52, step I) to perform step J) if the second voltage is greater than a fourth predetermined value (i.e., to examine whether the amount of biological sample is sufficient), otherwise perform step K), step J) to display the test result by the detection device 5 and terminate the testing procedure, step K) to display a warning message by the detection device 5 and terminate the testing procedure, and step L) to idle for two minutes and then terminate the testing procedure.

In the present embodiment, the first predetermined value is between 9 to 41° C., the second predetermined value is 0.58 or 1.01 volts (based on the background value of the device), the third predetermined value is 0.079 volts, the fourth predetermined value is 0.006 volts, and the driving voltage is higher than 0 volt but lower than 0.5 volts. If the above values are plugged into the method, the testing procedure would comprise step A of engaging the test strip with a detection device 5, in which the detection device 5 comprises a processor 52 and a temperature sensor 54. The testing procedure also comprises step B of detecting a first temperature of the test strip by the temperature sensor 54, step C of examining the first temperature by the processor 52, step D of performing step E if the first temperature is within the range of 9 to 41° C. which matches the working temperature for the present system, otherwise perform step K. The testing procedure further comprises step E of examining a first voltage of the first electrode 32 by the processor 52, step F of performing step G if the first voltage is below 0.58 or 1.01 volts (which indicates that the test strip is unused), otherwise perform step K, step G of loading a sample (the blood sample, in the present embodiment) to the inlet 12 on the test strip and provide a driving voltage in 0-0.5 volts (0.42 volts, in the present embodiment) by the detection device 5 to obtain a test result and store the test result to the memory unit 53 for step H if the first voltage is greater than 0.079 volts, otherwise perform step L, step H of examining a second voltage of the third electrode 36 by the processor 52, step I of performing step J if the second voltage is greater than 0.006 volts, otherwise perform step K, step J of displaying the test result by the detection device 5 and terminate the testing procedure, step K of displaying a warning message by the detection device 5 and terminate the testing procedure, and step L of idling for two minutes and then terminate the testing procedure.

Figure 7:
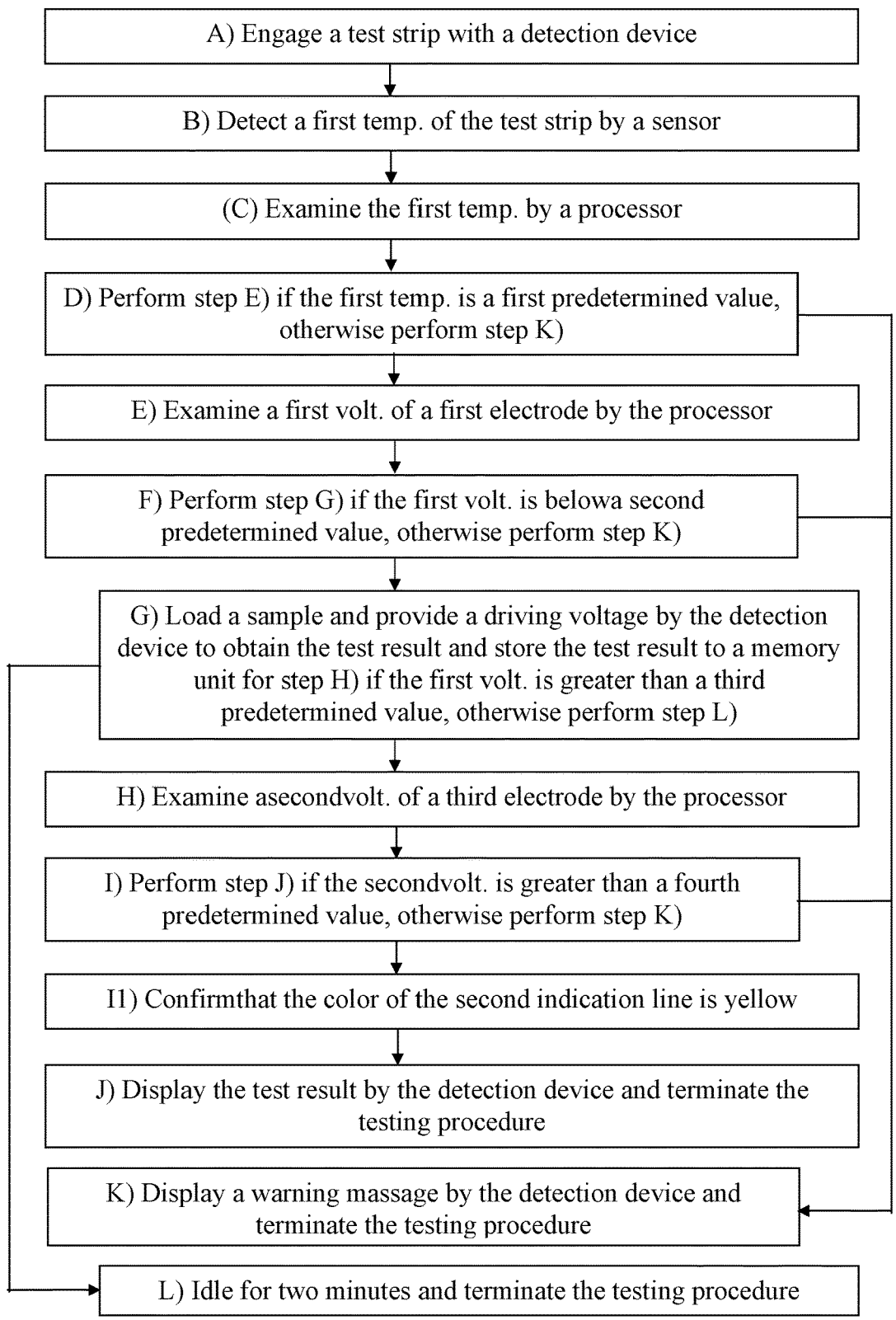
FIG. 7 is the flow chart of a method of operating test strip comprising a step of confirming, in accordance with some embodiments of the present invention.

In some alternate embodiments, users may confirm that whether the blood sample arrives at the first indication line 161 or the second indication line 162 in advance. Under these embodiments, step I1) is incorporated between step I) and step J) in the method as illustrated in FIG. 7. FIG. 7 is the flow chart of a method of operating test strip comprising a step of confirming. On the premise that the test strip comprises a second indication line 162 covered by a color developer and the blood sample is introduced, the step I1) is to confirm that the color of the second indication line is yellow before performing step J) and the subsequent steps.

Accordingly, the test strips and the methods of operating thereof in the present invention provide mechanisms for users to examine whether the test strip is unused and whether the amount of biological sample is sufficient before using the test strip. After the biological sample is introduced, the first electrode is used to activate the testing and the third electrode is used to confirm the amount of biological sample. These mechanisms can reduce errors and increase the accuracy of the testing.

There are many inventions described and illustrated above. The present inventions are neither limited to any single aspect nor embodiment thereof, nor to any combinations and/or permutations of such aspects and/or embodiments. Moreover, each of the aspects of the present inventions, and/or embodiments thereof, may be employed alone or in combination with one or more of the other aspects of the present inventions and/or embodiments thereof. For the sake of brevity, many of those permutations and combinations will not be discussed separately herein.

What is claimed is:

1. A test strip for biomaterials, comprising:
   a substrate, wherein the substrate is a layer of polyester;
   an electrode set disposed on the substrate, wherein the electrode set comprises a first electrode, a second electrode, and the third electrode;
   an insulating layer disposed on the electrode set, wherein the insulating layer comprises a track at one end of the insulating layer;
   a cover disposed on the insulating layer, wherein the cover comprises an inlet, a first indication line, a second indication line, and at least one vent;
   wherein the first electrode contains a first reaction region exposed to the track;
   wherein the third electrode contains a third reaction region exposed to the track;
   wherein the second electrode contains a second reaction region;
   wherein the first reaction region is configured at the outer area of the track, the third reaction region is configured at the inner area of the track, and the second reaction region is configured between the first reaction region and the third reaction region;
   wherein the inlet is disposed at one end of the cover close to the track;
   wherein the first indication line is configured at one end of the track away from the inlet, and the second indication line is located in the middle of the first indication line;
   wherein the at least one vent is configured with the first indication line away from the inlet;
   wherein the first indication line is coated with a dye; and
   wherein the second indication line is coated with a color developer, and the color developer is a temperature sensitive agent which changes color from violet to yellow under the range of 35 to 37° C.

2. The test strip as claimed in claim 1, wherein the first electrode is a working electrode.

3. The test strip as claimed in claim 1, wherein the second electrode is a reference electrode.

4. The test strip as claimed in claim 1, wherein the third electrode is an electrode-based fullness detector.

5. The test strip as claimed in claim 1, wherein the cover is transparent.

6. The test strip as claimed in claim 1, wherein the color developer comprises 3,3-bis-(4-dimethylaminophenyl)-6-dimethylaminophthalide.

7. The test strip as claimed in claim 1, wherein the color developer comprises bisphenol A.

8. A method of operating the test strip as claimed in claim 1, comprising the steps of:
- A) engaging the test strip with a detection device, wherein the detection device comprises a processor, a sensor, and a memory unit;
- B) detecting, by the sensor, a first temperature of the test strip of a working system;
- C) examining, by the processor, the first temperature of the test strip of the working system;
- D) performing step E) if the first temperature is within the range of 9 to 41° C., otherwise performing step K);
- E) examining, by the processor, a first voltage of the first electrode;
- F) performing step G) if the first voltage is below a second predetermined value, otherwise performing step K);
- G) loading a sample and providing, by the detection device, a driving voltage to obtain a test result and storing the test result to the memory unit for step H) if the first voltage is greater than a third predetermined value, otherwise performing step L);
- H) examining, by the processor, a second voltage of the third electrode;
- I) performing step J) if the second voltage is greater than a fourth predetermined value, otherwise performing step K);
- J) displaying, by the detection device, the test result and terminating the testing procedure;
- K) displaying, by the detection device, a warning message and terminating the testing procedure; and
- L) idling for two minutes and terminating the testing procedure.

9. The method as claimed in claim 8, wherein the second predetermined value is 1.01 volts.

10. The method as claimed in claim 8, wherein the second predetermined value is 0.58 volts.

11. The method as claimed in claim 8, wherein the third predetermined value is 0.079 volts.

12. The method as claimed in claim 8, wherein the fourth predetermined value is 0.006 volts.

13. The method as claimed in claim 8, wherein the driving voltage is higher than 0 volt but lower than 0.5 volts.

14. A method of operating the test strip as claimed in claim 1, comprising the steps of:
- A) engaging the test strip with a detection device, wherein the detection device comprises a processor and a sensor;
- B) detecting, by the sensor, a first temperature of a working system of the test strip;
- C) examining, by the processor, the first temperature of the working system of the test strip;
- D) performing step E) if the first temperature is within the range of 9 to 41° C., otherwise performing step K);
- E) examining, by the processor, a first voltage of the first electrode;
- F) performing step G) if the first voltage is below a second predetermined value, otherwise performing step K);
- G) loading a sample and providing, by the detection device, a driving voltage to obtain a test result and storing the test result to the memory unit for step H) if the first voltage is greater than a third predetermined value, otherwise performing step L);
- H) examining, by the processor, a second voltage of the third electrode;
- I) performing step J) if the second voltage is greater than a fourth predetermined value, otherwise performing step K);
- I1) confirming that the color of the second indication line changes to yellow under the range of 35 to 37° C.;
- J) displaying, by the detection device, the test result and terminating the testing procedure;
- K) displaying, by the detection device, a warning message and terminating the testing procedure; and
- L) idling for two minutes and then terminating the testing procedure.

15. The method as claimed in claim 14, wherein the second predetermined value is 1.01 or 0.58 volts, the third predetermined value is 0.079 volts, and the forth predetermined value is 0.006 volts.

16. The method as claimed in claim 14, wherein the driving voltage is higher than 0 volt but lower than 0.5 volts.

* * * * *